United States Patent [19]
Carroll et al.

[11] Patent Number: 6,066,146
[45] Date of Patent: May 23, 2000

[54] LAPARASCOPIC INCISION CLOSURE DEVICE

[76] Inventors: Brendan J. Carroll, 2278 Betty La., Beverly Hills, Calif. 90210; Jeffrey S. Kadan, 216 Via Linda Vista, Redondo Beach, Calif. 90277; Frederick Gotha, 957 Coronado Dr., Arcadia, Calif. 91006; Gregory M. Miles, 7055 Divot Dr., La Verne, Calif. 91750

[21] Appl. No.: 09/103,765

[22] Filed: Jun. 24, 1998

[51] Int. Cl.[7] .................................................. A61B 17/04
[52] U.S. Cl. ............................ 606/148; 606/144; 606/213
[58] Field of Search ................................... 606/148, 144, 606/145, 146, 147, 139, 140, 213–232

[56] References Cited

U.S. PATENT DOCUMENTS

| | | | |
|---|---|---|---|
| 5,085,661 | 2/1992 | Moss | 606/144 |
| 5,290,279 | 3/1994 | Phillips | 606/144 |
| 5,480,961 | 1/1996 | Jiang et al. | 528/220 |
| 5,507,754 | 4/1996 | Green et al. | 606/139 |
| 5,741,278 | 4/1998 | Stevens | 606/223 |
| 5,810,848 | 9/1998 | Hayhurst | 606/232 |

*Primary Examiner*—Michael Buiz
*Assistant Examiner*—Lien Ngo
*Attorney, Agent, or Firm*—Frederick Gotha

[57] ABSTRACT

A laparascopic incision closure device comprised of an ejector housing having finger holding rings and a thumb ring attached to a plunger shaft and plunger for sequentially ejecting T-bar sutures into a trocar site incision through a needle. T-bar sutures are ejected by operation of a trigger mounted in the ejector housing for quick and easy operation to eject a T-bar through fascia adjacent to a trocar site incision. Multiple T-bar sutures are stored in the interior of the ejector housing and needle for quick and easy placement through fascia on opposite sides of a wound. In the preferred embodiment the device is constructed of a disposable plastic material with sutures being formed of an absorbable material.

15 Claims, 11 Drawing Sheets

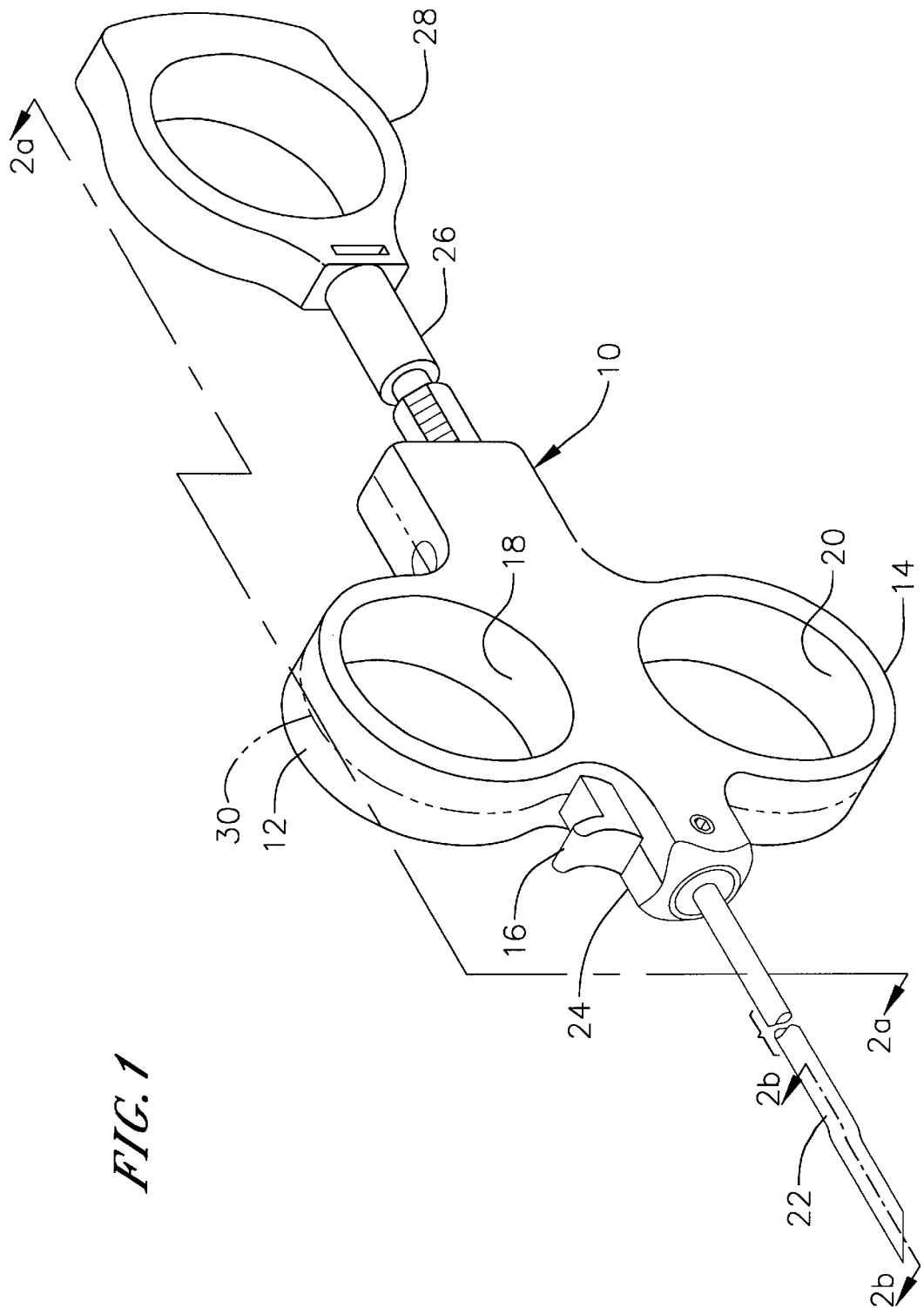

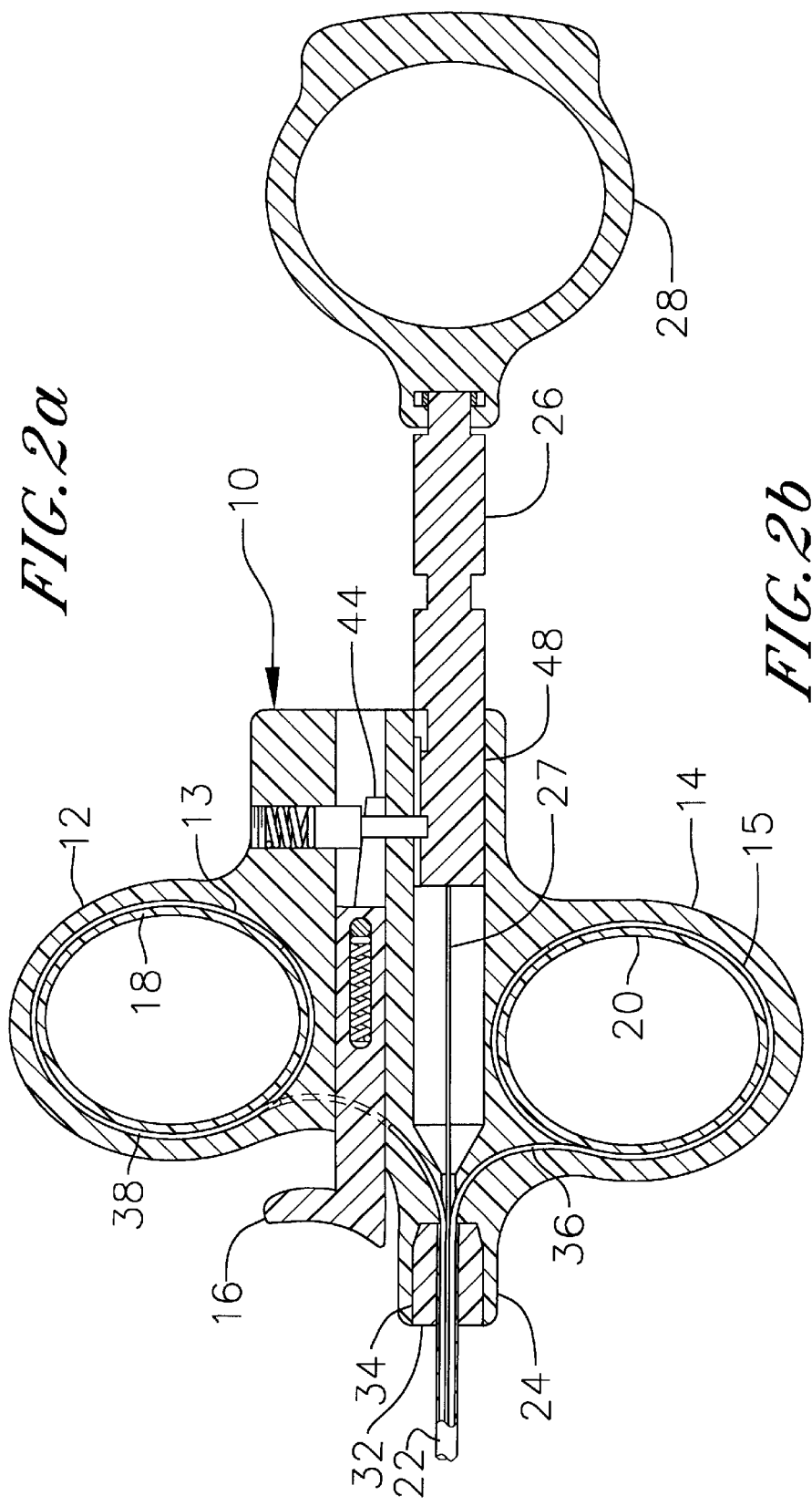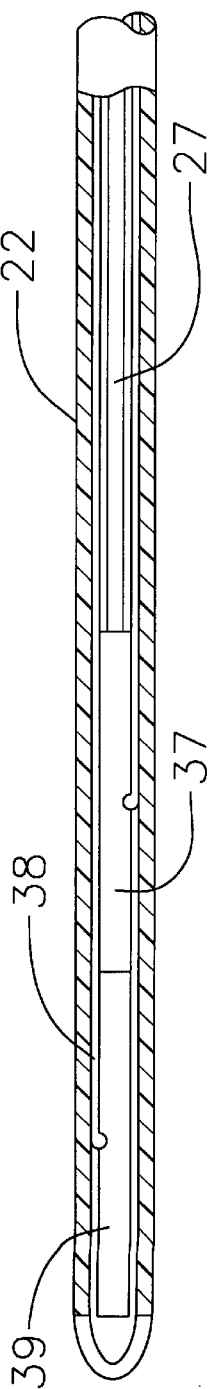

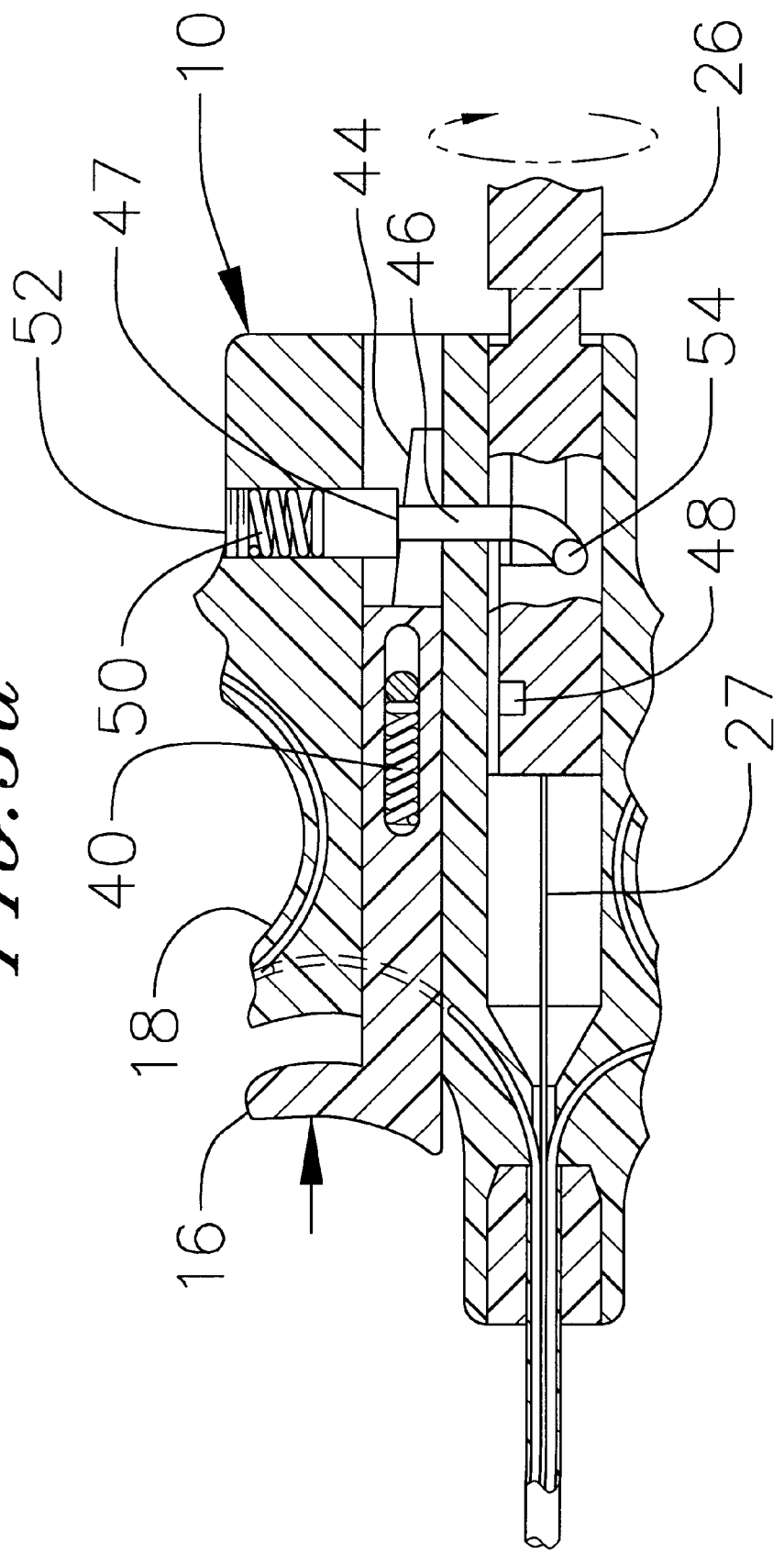

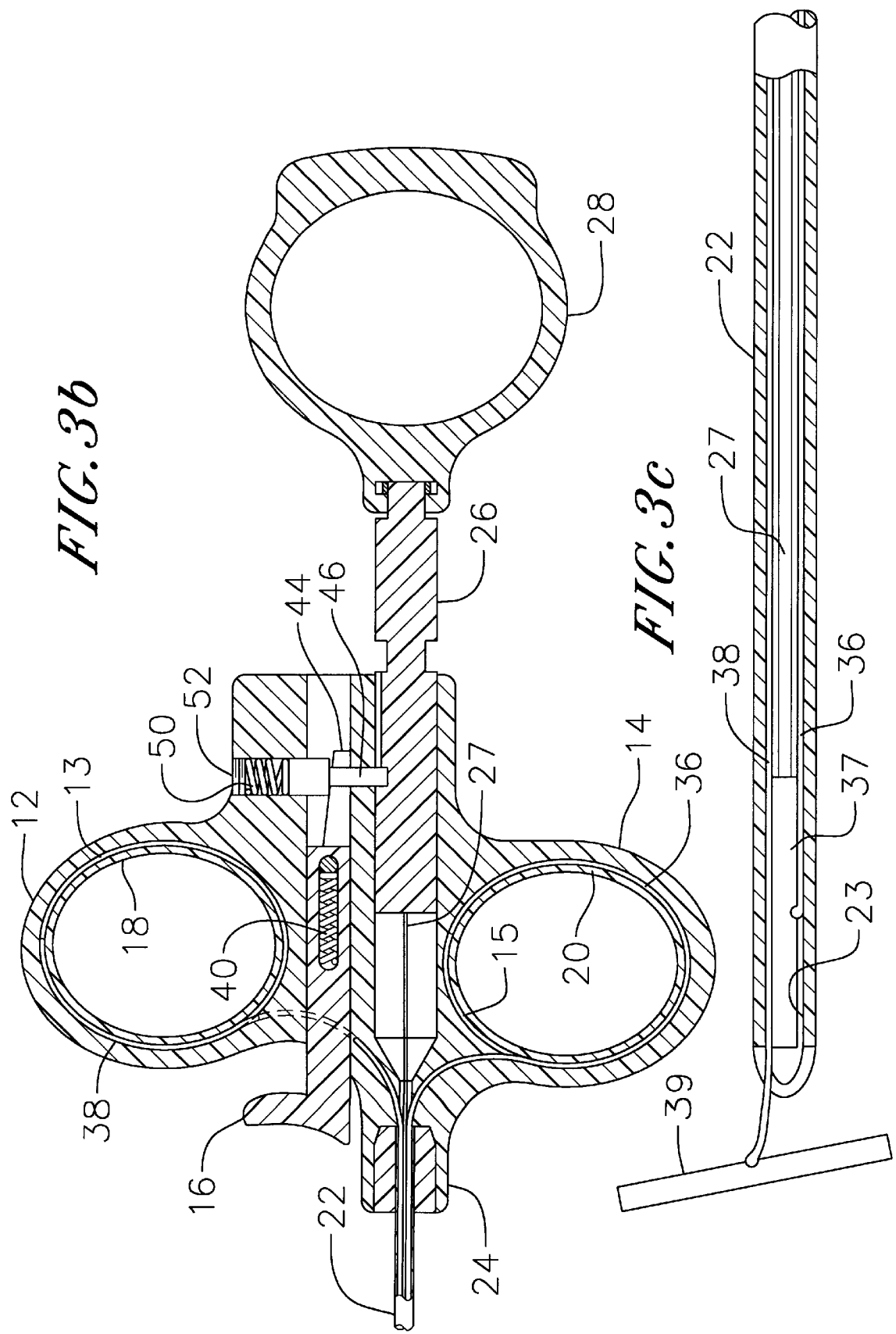

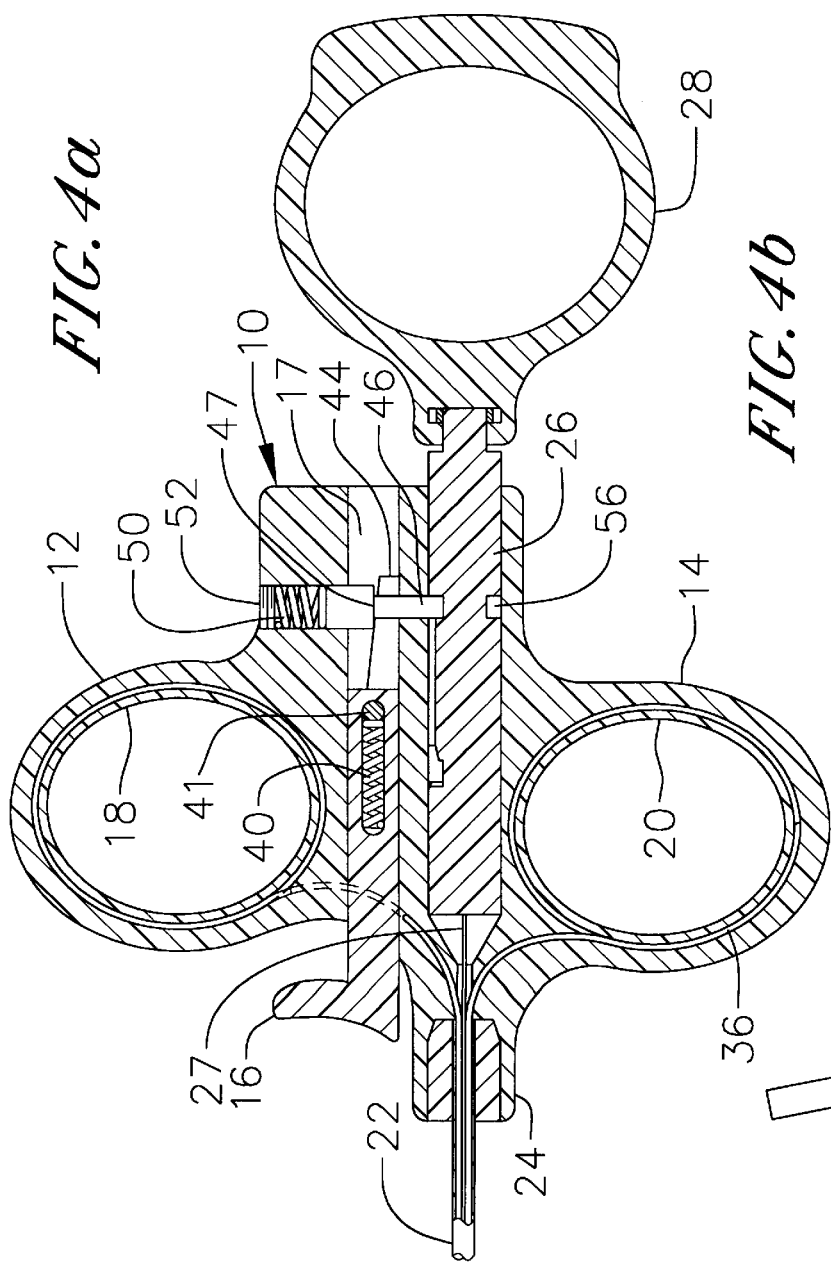
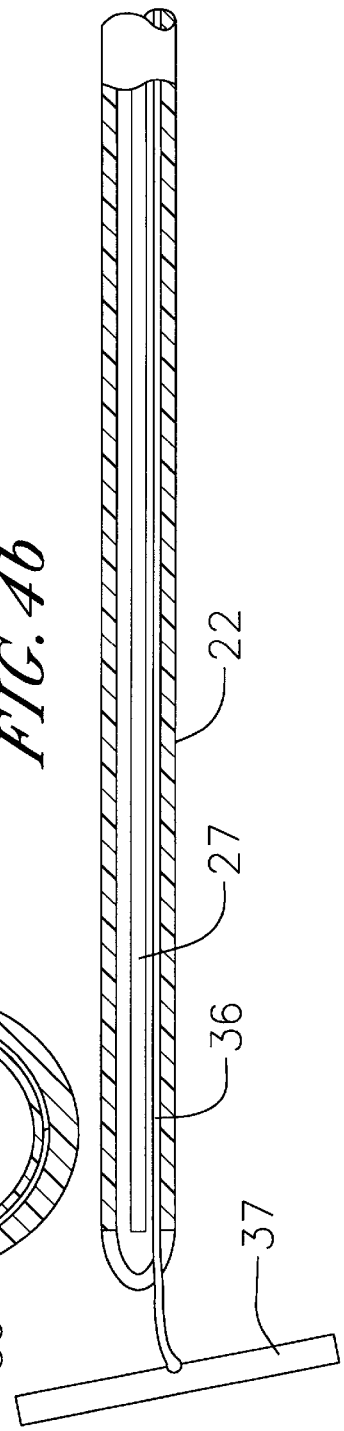
FIG. 4a
FIG. 4b

ID CLOSURE
LAPARASCOPIC INCISION CLOSURE DEVICE

BACKGROUND OF THE INVENTION

1. Field of the Invention

This invention relates to devices for placing sutures to close incisions and more particularly relates to a device and method to efficiently close small incisions used in laparascopic surgery.

2. Background Information

Laparascopic surgical procedures generally use small incisions some 5 to 16 millimeters in length for placement of a cannula and trocar used in laparascopic surgical procedures such as cholecystectomy, herniorrhaphy, Nissen, hysterectomy, colectomy, etc. One method used to close such incisions is by simple surface skin or facial closures. However, a not infrequent problem with this and other methods is that the closures are not affective enough and lead to complications such as hernias and bowel strangulations.

Another method used to close such incisions is by a tedious procedure that requires a surgeon to laparascopically grasp a suture from a closure insertion device after placement through the abdominal wall. The closure insertion device is then withdrawn and then reinserted through the abdominal wall on the opposite side of the trocar site incision. The surgeon must then reinsert the needle into the closure insertion device and then withdraw it creating a loop around the trocar site incision. The tedious part of the process is the need to reinsert the suture into the closed insertion device which sometimes requires a surgeon to "work backwards" depending on the camera location.

Thus there is a need for a simple and preferably disposable device for closure of trocar site incisions used in laparascopic surgical procedures described above. A device that could quickly, efficiently and atraumatically insert sutures to close a laparascopic incision would be advantageous.

There is an existing device called a Brown/Mueller Fastener described in U.S. Pat. No. Re. 34,021 of Peter R. Mueller et al, that is designed to insert a T-bar fastener through the abdominal wall. This device has a needle with a slot in the end for receiving a metal T-bar with a single short suture extending through the slot along the outside of the needle. The needle with the loaded metal T-bar and short suture is then inserted through the abdominal wall. The metal T-bar and attached suture is then extruded from the needle allowing the metal T-bar to fasten the suture inside the abdomen. This device is currently used for securing a portion of an intestine to the abdominal wall for placement of feeding tubes. A disadvantage of this device is that it allows placement of only a single suture which must be securely held by the surgeon while the needle is piercing the abdomen.

It is therefore one object of the present invention to provide laparascopic insertion/closure device that can quickly and efficiently place multiple T-bar sutures on opposite sides of a trocar site incision to close the wound.

Another object of the present invention is to provide a laparascopic incision closure device that can store multiple T-bar sutures inside a housing.

Still another object of the present invention is to provide a laparascopic incision closure device having an ejection mechanism for firing and ejecting one T-bar suture at a time.

BRIEF DESCRIPTION OF THE INVENTION

The purpose of the present invention is to provide a laparascopic incision closure device and method for quickly and efficiently placing multiple T-bar sutures on opposite sides of a trocar site incision to close defectos left by the incision.

The laparascopic incision closure device is particularly designed and adapted to close small incision use in laparascopic surgeon such as cholecystectomy, herniorrhaphy, Nissen, Hysterectomy, colectomy, and the like. These incisions are generally 5 to 16 millimeters in length and allow instruments to be passed through the abdominal wall through a cannula. The defect left by these incision must be closed to prevent development of complications such as hernia and bowel strangulation.

The laparascopic incision closure device is comprised to an ejector housing having finger gripping holes and a needle extending from the end of the housing. The needle is preferably about 18 millimeters. Multiple T-bar sutures are stored in the needle with the suture extending up the needle and stored inside the ejector housing. In one embodiment the sutures extend into the housing and wrap around inside the rings forming finger gripping holes.

A plunger extending through the needle ejects T-bar sutures one at a time by activation of a trigger that fires and releases a plunger shaft pushed forward by the thumb placed in a thumb ring on the end of the shaft. When loaded the plunger shaft position is locked by a spring operated pin. The pin engages a slot in the side of the plunger shaft.

The trigger is preferably mounted in the housing below the rings forming the finger handles. The trigger has a tapered end forming a cam that engages a shoulder on the locking trigger pin to dislodge the pin from the plunger shaft allowing the plunger shaft to move forward pushing the plunger along the needle to eject a T-bar suture. A second socket along the plunger shaft locks the trigger with the plunger in position for ejecting another T-bar suture from the needle.

To place a second T-bar suture the locking pin is again released from the second socket by operation of the trigger allowing the plunger shaft to be retracted by the thumb in the thumb ring. This positions a second T-bar suture for ejection from the needle. As the plunger shaft is retracted the locking plunger and pin slide along a groove in the trigger shaft and again lock in a first socket ready for repeat operation.

In a second less preferred embodiment the trigger is a rotatable lever or button above the finger rings in the ejector housing having a pointed end engages detents in the plunger shaft. The trigger is pivotally mounted on a pin and has a tip that is biased into engagement with detents on the plunger shaft by a spring. To operate the device the trigger button is pushed or tilted toward the ejector housing releasing the tip from a plunger shaft detent allowing the plunger shaft to advance advancing the plunger to eject a T-bar suture. A second detent in the trigger shaft re-engages the trigger when the T-bar suture is ejected. To place another suture the trigger button is again operated allowing the plunger shaft to be further advanced by the thumb ring positioning the suture plunger in the needle for ejection of a second T-bar suture.

The laparascopic incision closure device is preferably constructed of a disposable plastic material with multiple T-bar sutures loaded in the housing and wrapped around the finger rings. Optionally the sutures could extend through ports on either side of the housing into the ejector needle.

Preferably the sutures are placed with a cannula in place in a laparascopic incision. The sutures are also preferably made of an absorbable material such as an "O-Vicryl" suture attached to an absorbable T-bar made of material similar to that used in "Absalock Clips" such as polydioxone. The T-bar sutures are placed on either side of a trocar incision under direct visualization. Preferably the laparascopic incision closure device needle is inserted through the fascia on one side of the wound with the cannula still in place. The needle is then withdrawn leaving the T-bar suture in place through the fascia. The needle is then inserted through the fascia of the opposite side of the wound and a second T-bar suture ejected. With the cannula removed the sutures then can be tied over the fascia defect externally. Thus all surgeon needs to do is insert T-bar sutures through the fascia on either side of the cannula in the trocar site then tie the two sutures over the defect. The closure is very simple and cost effective.

The above and other novel features of the invention will be more fully understood from the following detailed description and the accompanying drawings, in which:

BRIEF DESCRIPTION OF THE DRAWINGS

FIG. 1 is an isometric view of one embodiment of laparascopic incision closure device according to the invention.

FIG. 2a is a sectional view taken at 2a 2a of FIG. 1.

FIG. 2b is a sectional view taken at 2b 2b of FIG. 1.

FIG. 3a is an enlarged partial sectional view illustrating the operation of the trigger firing mechanism.

FIG. 3b is a partial sectional view illustrating the laparascopic incision closure device in position for ejecting a second suture.

FIG. 3c illustrates the ejection of the first suture and the device in position for ejecting a second suture.

FIG. 4a is a sectional view illustrating operation of the device for ejecting a second suture.

FIG. 4b is a partial sectional view illustrating the ejection of the second suture.

DETAILED DESCRIPTION OF THE INVENTION

Figure 5:
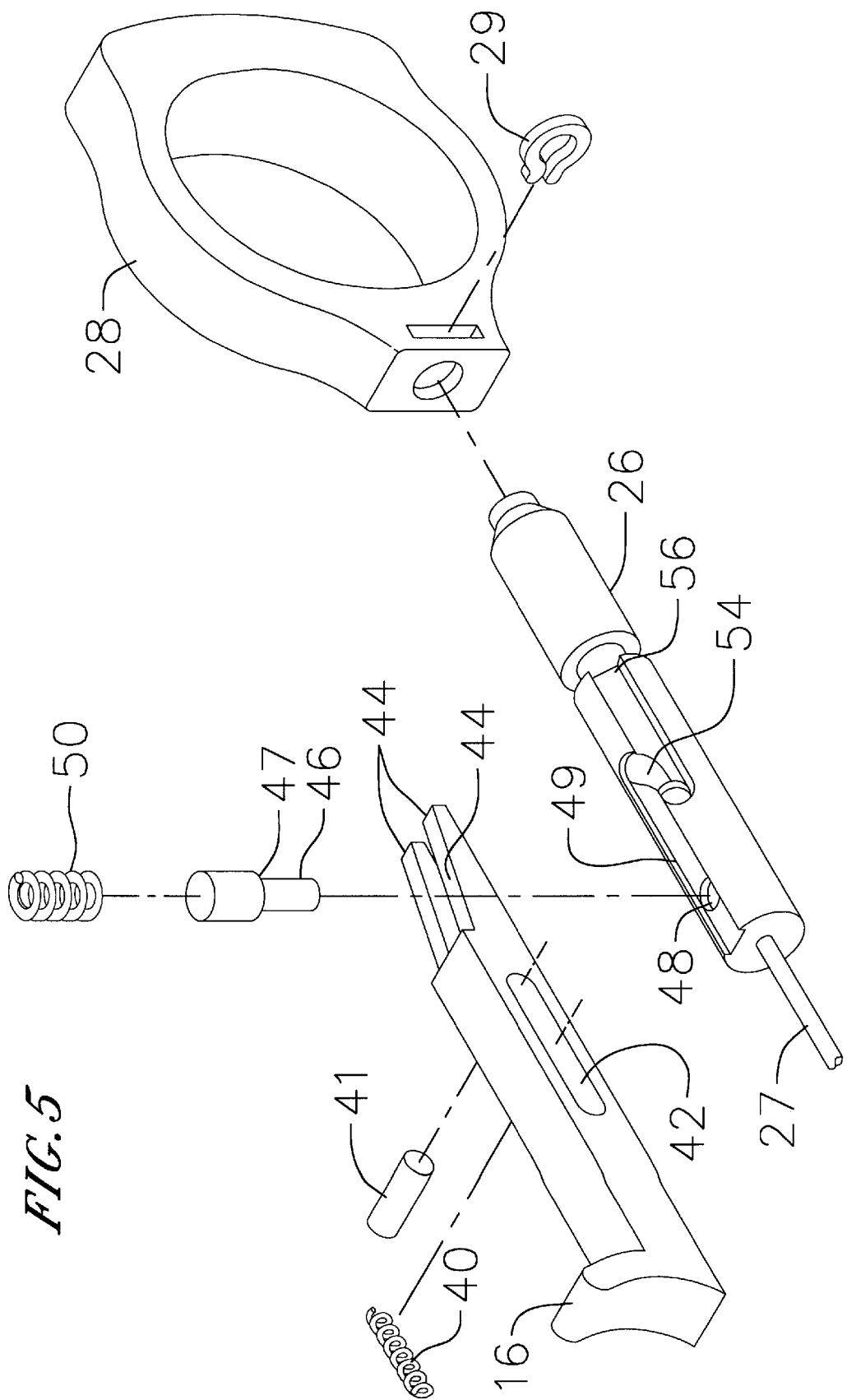
FIG. 5 is an exploded view illustrating the construction of the trigger mechanism and trigger shaft.

A laparascopic incision closure device is shown in the isometric view of FIG. 1 and is comprised of an ejector housing 10 having finger rings 12 and 14 and a firing trigger 16. Finger rings 12 and 14 have finger holes 18 and 20 for use in operating the laparascopic incision closure device as will be described in greater detail hereinafter. A needle 22 is securely attached to an ejector housing extension 24 for ejecting a T-bar suture into the fascia of a wound as will also be described in greater detail hereinafter.

T-bar sutures are ejected by a plunger operated by plunger shaft 26 and thumb ring 28. Preferably ejector housing 10 is made of a disposable material such as a plastic in a clam shell construction indicated by dotted line 30.

The internal construction of the laparascopic incision closure device is illustrated in FIGS. 2a and 2b. Needle 22 is securely attached to housing extension 24 by a boss 32 in a socket 34 securely clamped by Allen screw 36 (FIG. 1). Needle 22 holds multiple T-bar sutures 36 and 38 and plunger 27 attached to plunger shaft 26. Sutures 36 and 38 wind around circular cavities 13 and 15 in finger rings 12 and 14 and extend down needle 22. T-bar 39 on the end of suture 38 is positioned for ejection from the tip of needle 22 by the end of plunger 27. The device is illustrated with only two sutures in FIGS. 2a and 2b but a plurality of sutures can be provided if desired.

Suture 38 with T-bar 39 is ejected from needle 22 by pressing downward on thumb ring 28 as will be described in greater detail hereinafter. The firing mechanism is comprised of a trigger 16 biased by a spring 40 in slot 42. Trigger 16 is a shaft 17 having fingers 44 forming a cam that engages shoulder 47 on trigger locking pin 46 biased into engagement with socket 48 in plunger shaft 26 by spring 50 as shown in greater detail in FIG. 3a. Trigger 16 is slidably mounted in bore 17 through ejector housing 10 and is held in position by pin 41 and biasing spring 40 in slot 42 in the trigger shaft.

The tapered cam surface on fingers 44 engage shoulder 47 on trigger locking pin 46. Trigger locking pin 46 is secured in ejector housing by Allen screw 52. When trigger 16 is pressed as indicated by the arrow the cam surface on fingers 44 engage shoulder 47 on locking pin 46 retracting it from socket 48 in trigger shaft 26 allowing plunger shaft 26 and plunger 27 to move forward until it reaches a stop position in a second socket 54. At this point the first T-bar 39 of T-bar suture 38 is ejected from the end of needle 22 as will be described in greater detail hereinafter. Preferably needle 22 is as an 18 millimeter bore 23 that will hold at least two T-bar sutures 36 and 38.

Release of a second suture from needle 22 is illustrated in the sectional views of FIG. 4a and 4b. To release the second suture trigger 16 is again operated allowing the cam surface on fingers 44 to engage shoulder 47 of locking pin 46 releasing it from socket 54 allowing trigger shaft 26 and plunger to advance ejecting a second T-bar 37 on suture 36 from needle 22. Locking pin stops at annulus 56 in plunger shaft 26.

The details of the trigger mechanism are shown in the exploded view of FIG. 5. Trigger 16 is held in ejector housing 10 by pin 41 and spring 40 engaging slot 42. The end of trigger 16 has a pair of fingers 44 forming cam surface 45 that engages shoulder 47 on locking pin 46. Locking pin 46 locks the trigger shaft 26 by engaging socket 48 in axial groove 49. Release of locking pin 46 from socket 48 allows plunger shaft 26 to move forward until locking pin 46 engages socket 54. A further operation allows locking pin 46 to move along a continuation of slot 49 into annulus 56 to eject the second T-bar suture. Thumb ring 48 is attached to the end of trigger shaft by C-ring 29.

Figure 6A:
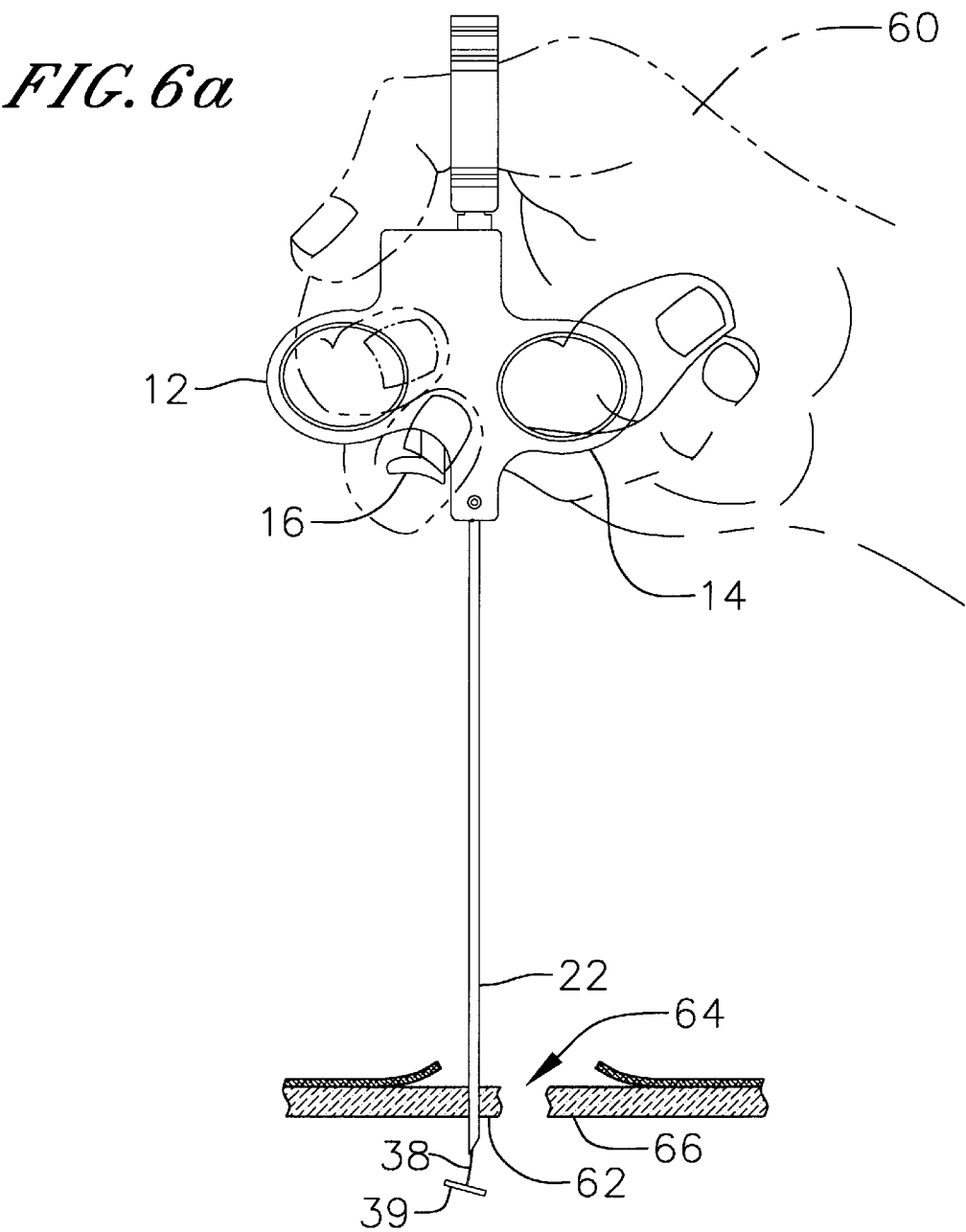
FIGS. 6a through 6c illustrate the operation of the laparascopic incision closure device.
Figure 6B:
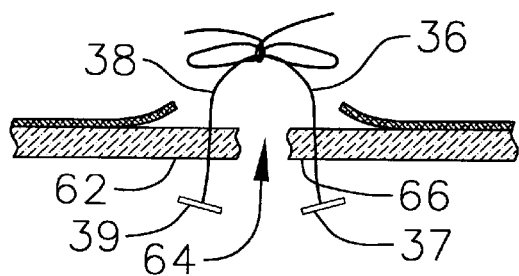
Figure 6C:
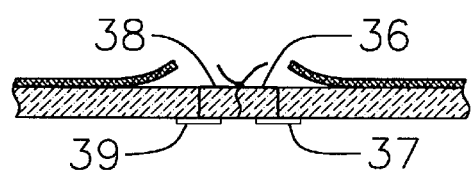

The operation of the device to release T-bar sutures on the opposite sides of a defecto at a surgical site is illustrated in FIGS. 6a through 6c. The surgeon 60 grips the laparascopic incision closure device with the index and third fingers engaging finger rings 12 and 14 respectively and the middle finger positioned to activate trigger 16. With the laparascopic incision closure device in this position, needle 22 is inserted through fascia 62 on one side and incision 64. When needle 22 has passed completely through fascia 62, trigger 16 is fired allowing plunger shaft 26 and thumb ring 28 to move forward causing plunger 27 to eject T-bar 39 on suture 38. Withdrawal of needle 22 leaves suture 38 in place through fascia 62 with T-bar 39 against the abdominal wall.

This procedure is repeated in fascia 66 on the opposite side of incision 64 placing a second suture 37 with T-bar 38 through the abdominal wall. Preferably sutures 36 and 38 are a O-Vicryl sutures attached to absorbable T-bars 37 and 39 respectively made of a material similar to that used in "Absalock Clips" such as polydioxone. Optionally the T-bars could be made of titanium. With T-bar sutures 36 and 38 placed on opposite sides of the defecto in incision 64 they are then tied over the fascial defect externally closing the wound as illustrated in FIG. 6*c*. Preferably sutures 36 and 38 are placed on opposite sides of the incision 64 while the cannula is still in place. After placement the cannula is then removed and the sutures 36 and 38 tied externally to close the wound.

Figure 7:
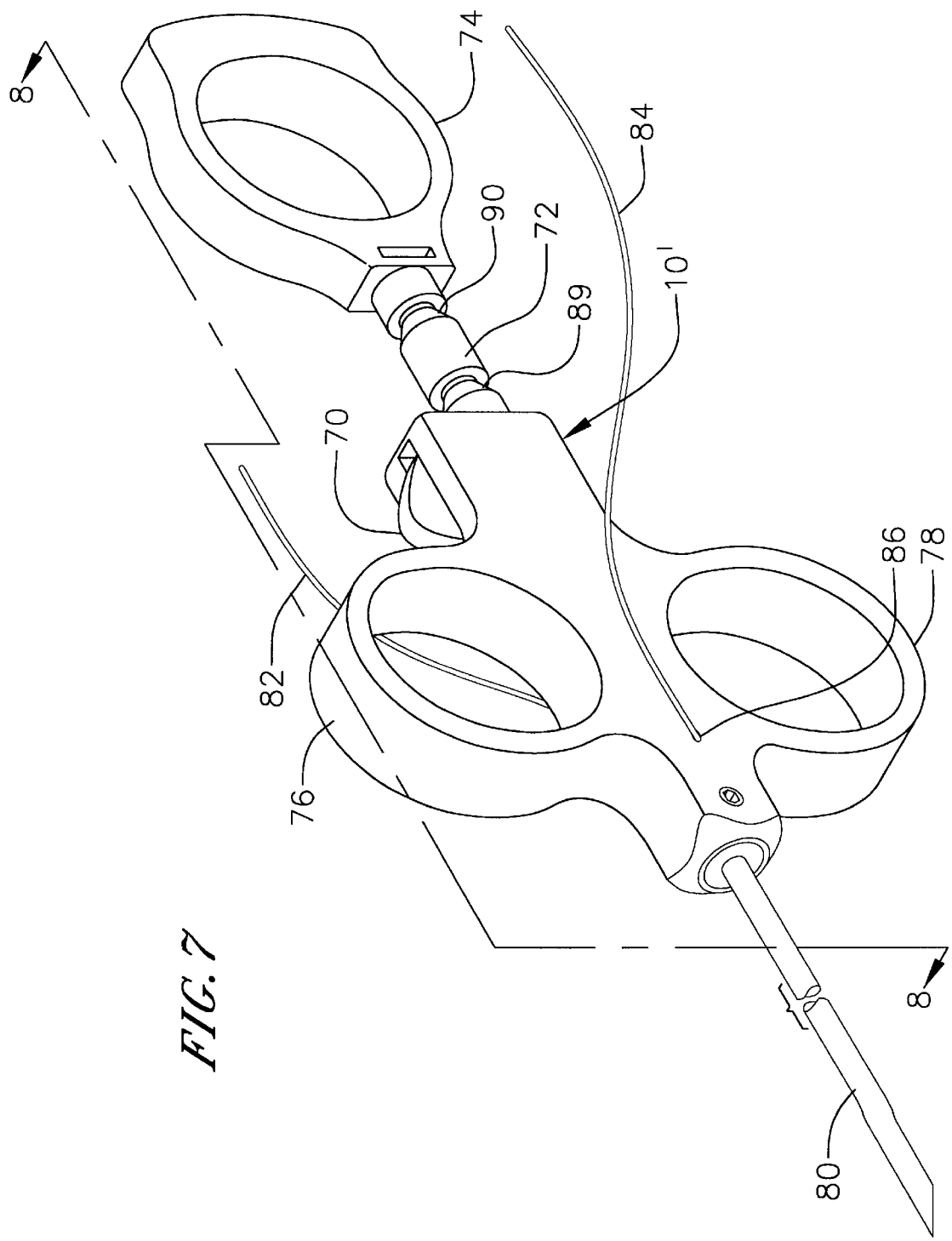
FIG. 7 is an isometric view of an alternate embodiment of the invention.

An optional embodiment of the laparascopic incision closure device is illustrated in FIG. 7. In this embodiment ejector housing 10' has a button trigger 70 engaging a plunger shaft 72 having thumb ring 74. Finger gripping rings 76 and 78 are provided as previously described. This design requires operation by thumb in ring 74 and the middle and ring finger in finger rings 76 and 78. Button triggers 70 would be operated by the index finger.

Needle 80 is attached to ejector housing 10 as described previously and has multiple T-bar sutures 82 and 84 loaded in through ports 86 and 87 into needle 80. In this embodiment, T-bar sutures 82 and 84 are loaded through ports 86 and 87 on opposite sides of the ejector housing 10' rather than being in positioned internally as in the previous embodiment.

Figure 8:
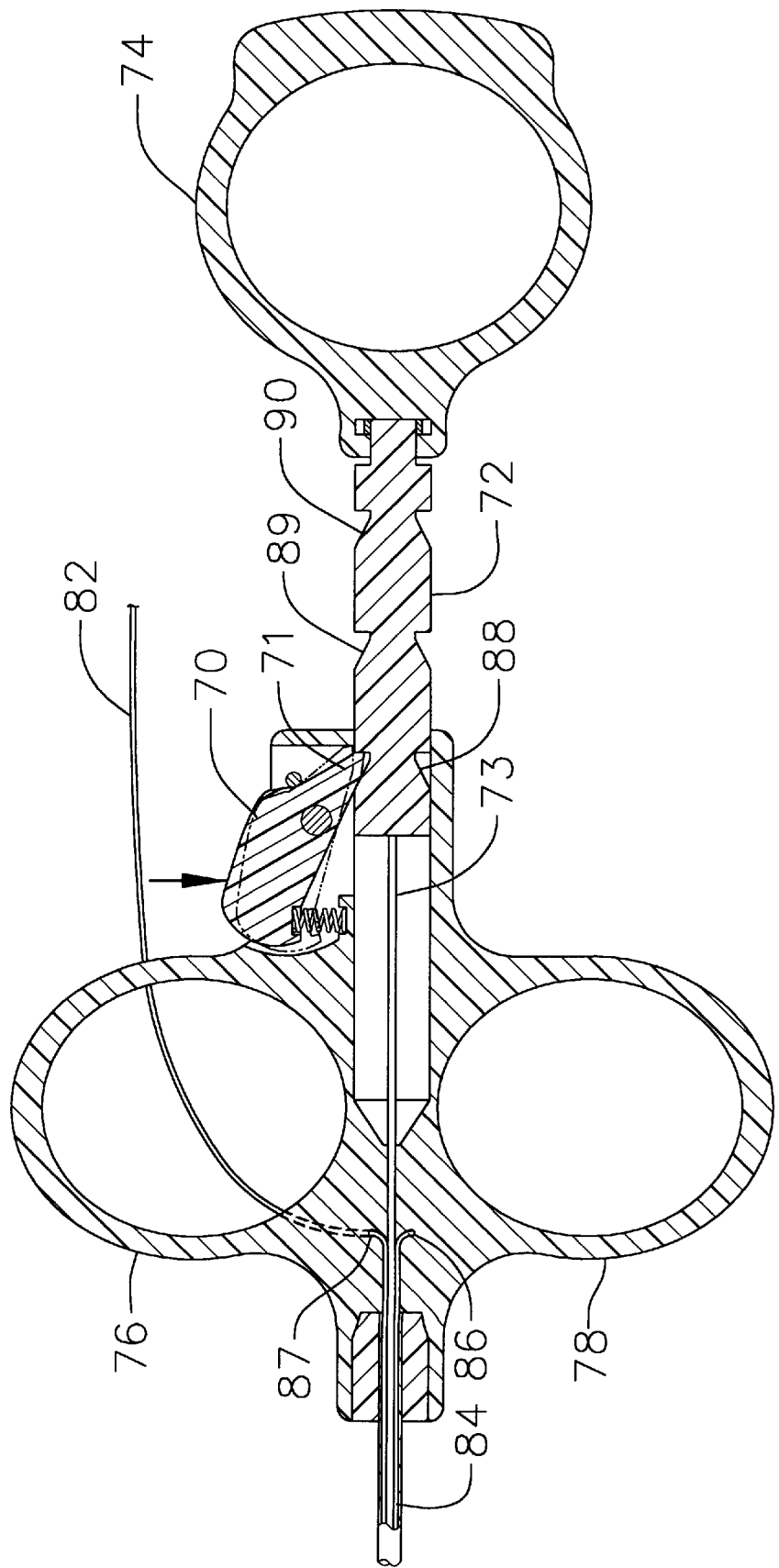
FIGS. 8, 9 and 10 are partial sectional views taken at 8—8 of FIG. 7 illustrate operation of the trigger mechanism of the second embodiment.
Figure 9:
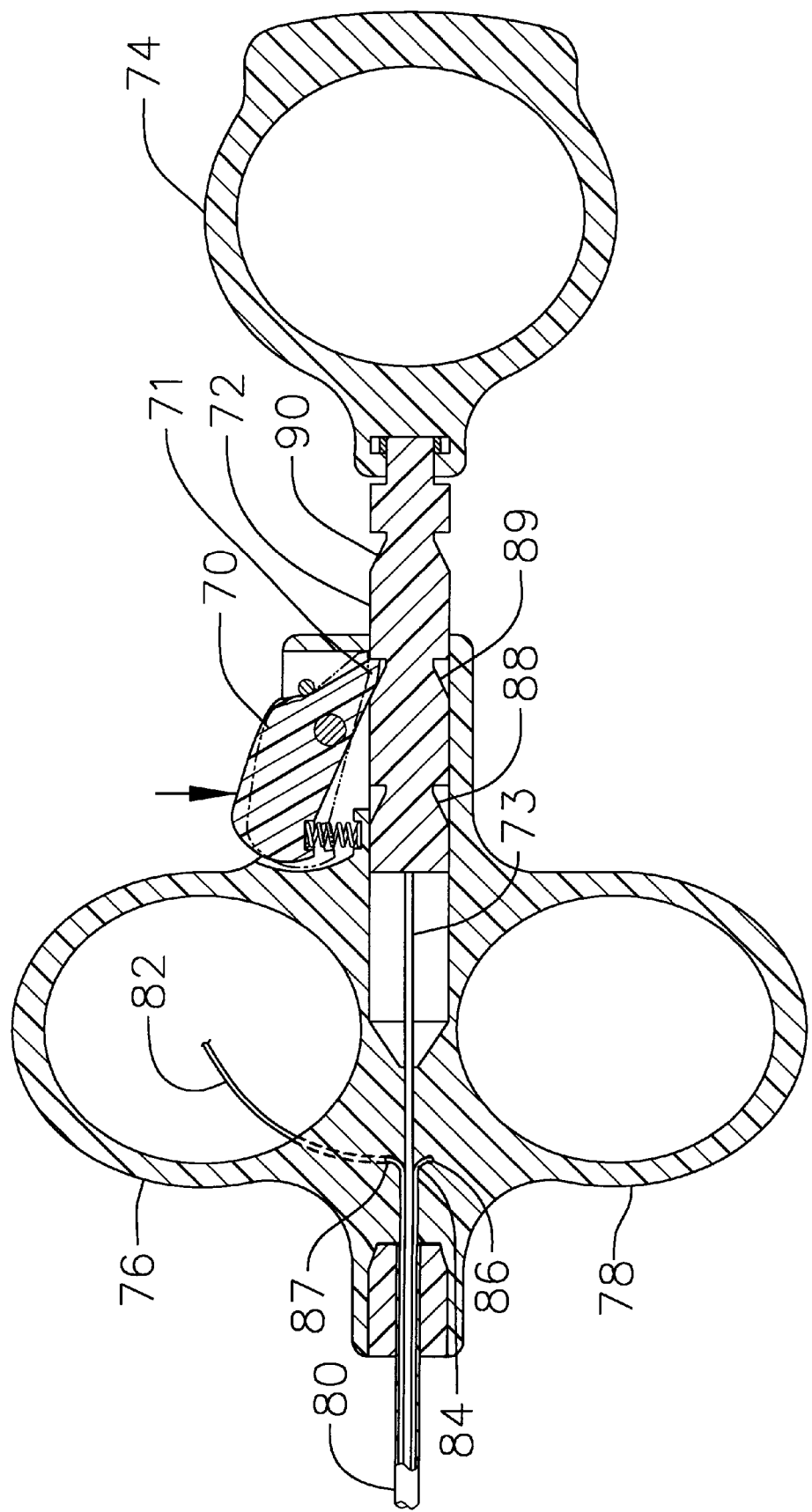
Figure 10:
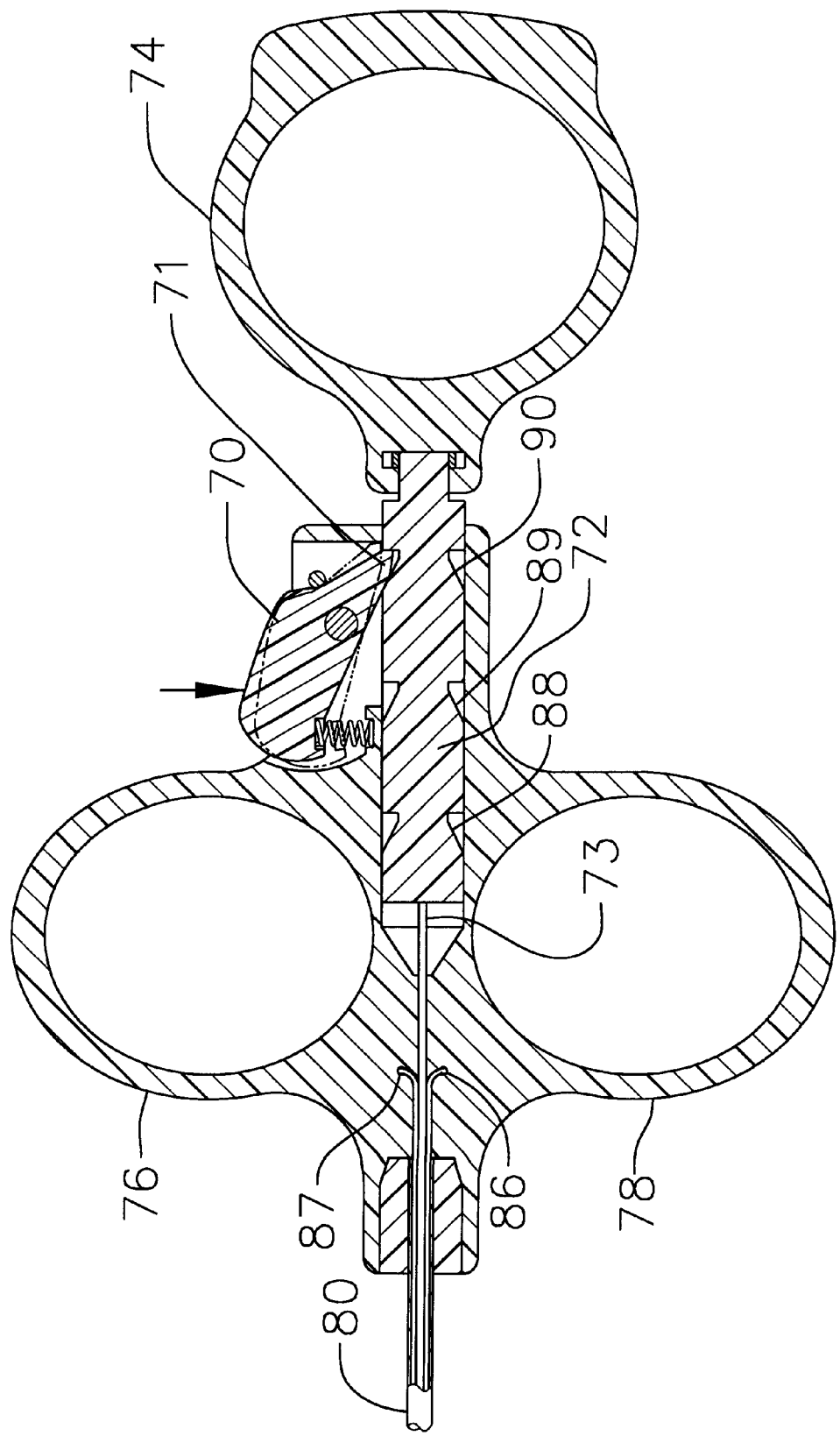

The operation of the button trigger laparascopic incision closure device is illustrated in FIGS. 8, 9 and 10. T-bar sutures 82 and 84 are positioned in needle 80 as shown in FIG. 2*b* with T-bars 37 and 39 positioned for ejection into the fascia of the wound. As shown in FIGS. 8 through 10 plunger shaft 72 is attached to plunger 73 which will eject T-bar sutures 82 and 84 from the end of needle 80. To operate this device the thumb is placed in thumb ring 74 and preferably the middle and ring fingers in finger holding rings 76 and 78. With the index finger trigger 70 is "fired" to dislodge trigger pin 71 from a first detent 88 in trigger shaft 70. This allows plunger shaft 72 and plunger 73 to move forward to eject a first T-bar suture through the fascia as illustrated in FIG. 6*a*.

Pin 71 on trigger 70 then engages second detend 89 in plunger shaft 72 stopping in this position as shown in FIG. 9. The laparascopic incision closure device is then removed from the fascia leaving the T-bar suture 82 in place. In this position the device is ready for placement of a second suture on the opposite side of an incision 64. Needle 80 is again inserted through fascia 66 on opposite side of incision 64 and trigger 70 fired again by an index finger dislodging trigger pin 71 from detend 89. This ejects a second T-bar suture 84 from the end of needle 80. Trigger pin 71 then stops in the third detend 90 in trigger shaft 72. The laparascopic incision closure device is then withdrawn leaving the second suture 84 in place in fascia 66. Sutures 82 and 84 are then tied closing wound 64.

Preferably the laparascopic incision closure device would be constructed of disposable material with sutures 82 and 84 of an absorbable material that dissolves over a period of time. Optionally the embodiment of FIGS. 8 and 9 could be constructed for re-use by re-loading T-bar sutures through ports 86 and 87 into needle 80. Reloading the laparascopic incision closure device is achieved by pressing button trigger 70 to remove plunger shaft 72 and plunger 73 from ejector housing 10'. Additional sutures can then be reloaded through ports 86 and 87 into needle 80 as desired.

Thus there has been disclosed a unique laparascopic incision closure device that can be used to place multiple sutures in detectos at trocar site incisions. The device has an ejector housing and needle for storing multiple sutures that can be quickly and easily placed through the fascia on opposite sides of the defecto in a trocar site incision. In the preferred embodiment the laparascopic incision closure device has a convenient finger and thumb rings and a trigger for firing the device to eject a T-bar suture through the fascia adjacent to an incision. The needle is then withdrawn from the fascia leaving the T-bar suture in place and inserted through the fascia on the opposite side of the incision and fired again by operation of a trigger to place a second T-bar suture. The sutures are then tied off closing a wound. In the first embodiment of the trigger is an L-shaped lever positioned for easy operation by the middle finger of the hand to fire the device to eject each T-bar suture.

In another embodiment the trigger is a button trigger at the upper end of the ejector housing for operation by an index finger to sequentially eject T-bar sutures through the fascia on opposite sides of the wound. The device is simple in construction and provides multiple sutures for quick and easy placement and secure closure of laparascopic incisions to prevent complications such as hernia and bowel strangulations.

This invention is not to be limited by the embodiment shown in the drawings and described in the description which is given by way of example and not of limitation, but only in accordance with the scope of the appended claims.

What is claimed is:

1. A Laparascopic incision closure device comprising:
   a housing;
   a needle having a longitudinal axis a proximal and distal end, and an axially extending longitudinal bore therethrough where said needle has a radial distal opening in said distal end and a radial proximal opening in said proximal end and where said longitudinal bore communicates with said radial distal opening and said radial proximal opening forming a continuously bounded passageway, and where said needle is attached to said housing at said proximal end,
   a plurality of T-bar sutures where each said T-bar suture comprises a T-bar portion and a suture portion integrally connected, and where said suture portion is so adapted and disposed in said housing and said longitudinal bore so as to permit axial passage of said T-bar portion and said suture portion through said longitudinal bore, and where said plurality of T-bar sutures are stored in said housing and said longitudinal bore;
   ejection means for sequentially ejecting said T-bar portion and said suture portion through said radial distal opening and through tissue adjacent to an incision;
   whereby a Laparascopic incision can be quickly and efficiently closed by sequential placement of a T-bar suture on opposite sides of said incision and then tying said respective suture portions to close the wound.

2. The device according to claim 1 in which said ejection means comprises a plunger mechanism for advancing said T-bar portion and said suture portion axially within said longitudinal bore and for ejecting a single T-bar suture out of said radial distal opening and trigger means for releasing said plunger mechanism whereby a T-bar Portion and suture portion of a T-bar suture is ejected from said longitudinal bore.

3. The device according to claim 2 wherein said plunger mechanism comprises a plunger coaxial with said longitudinal bore having an end engaging a T-bar suture loaded in said longitudinal bore, a plunger shaft attached to said plunger and slidably mounted in said housing; and operating means for moving said plunger shaft and plunger forward or backward in said housing.

4. The device according to claim 3 in which said operating means comprises a thumb ring on an end of said plunger shaft.

5. The device according to claim 4 in which said trigger means comprises; a trigger shaft slidable in said housing; lock means for locking said plunger shaft with said plunger in a ready position; and release means for releasing said locking means to fire said plunger shaft with said plunger to eject a T-bar attached to a suture out of said needle.

6. The device according to claim 5 in which said lock means comprises a trigger pin engaging a socket on said plunger shaft; and a spring biasing said lock pin into engagement with said socket; said release means dislodging said pin from said socket when said trigger is activated.

7. The device according to claim 6 in which said release means comprises a cam surface on said trigger shaft engaging a shoulder on said trigger locking pin whereby operation of said trigger releases said locking pin.

8. The device according to claim 7 in which said housing having finger gripping holes; said trigger being adjacent to and below said finger griping holes to facilitate operation by a middle finger.

9. The device according to claim 8 in which said T-bar sutures are made from an absorbable material.

10. The device according to claim 2 in which said Trigger means comprises a pivotally mounted button, said pivotally mounted button having a tip engaging a detent in said plunger shaft, and a spring biasing and holding said tip in said detent to lock said plunger shaft.

11. The device according to claim 10 in which said plunger shaft has a plurality of spread-apart detents for sequentially discharging multiple T-bar fasteners.

12. The device according to claim 8 in which said fingering gripping rings form substantially circular cavities; said T-bar sutures being stored by wrapping around said finger gripping rings in said cavities.

13. The device according to claim 1 in which said housing has ports communicating with said radial proximal opening of said longitudinal bore, said suture portions stored in said housing and said longitudinal bore extending out through said ports.

14. The device according to claim 13 in which said plurality of T-bar sutures is two T-bar sutures.

15. The device according to claim 12 in which said plurality of T-bar sutures is two T-bar sutures.

* * * * *